(12) United States Patent
Pagis et al.

(10) Patent No.: US 12,083,198 B2
(45) Date of Patent: Sep. 10, 2024

(54) USE OF FINE PARTICLE SIZE CALCINED KAOLIN AS AN OPACIFIER IN COSMETICS

(71) Applicant: IMERTECH SAS, Paris (FR)

(72) Inventors: Laure Pagis, Toulouse (FR); Anabelle Huguette Renée Legrix, St. Austell (GB); Victoria Michell, St. Austell (GB)

(73) Assignee: Imertech SAS, Paris (FR)

( * ) Notice: Subject to any disclaimer, the term of this patent is extended or adjusted under 35 U.S.C. 154(b) by 0 days.

(21) Appl. No.: 16/917,298

(22) Filed: Jun. 30, 2020

(65) Prior Publication Data

US 2021/0000711 A1    Jan. 7, 2021

Related U.S. Application Data

(63) Continuation of application No. 16/092,082, filed as application No. PCT/EP2017/058310 on Apr. 6, 2017, now abandoned.

(30) Foreign Application Priority Data

Apr. 8, 2016 (EP) ..................... 16305412
Aug. 31, 2016 (EP) ..................... 16306098

(51) Int. Cl.
C11D 9/20 (2006.01)
A61K 8/26 (2006.01)
A61Q 5/00 (2006.01)
A61Q 19/00 (2006.01)
A61Q 19/10 (2006.01)

(52) U.S. Cl.
CPC ............... *A61K 8/26* (2013.01); *A61Q 5/00* (2013.01); *A61Q 19/00* (2013.01); *A61Q 19/10* (2013.01); *A61K 2800/26* (2013.01)

(58) Field of Classification Search
CPC ... C11D 3/0089; C11D 3/0094; C11D 3/1253; C11D 3/14; C11D 9/18; C11D 9/20
See application file for complete search history.

(56) References Cited

U.S. PATENT DOCUMENTS

| | | | |
|---|---|---|---|
| 2,979,685 A | 4/1961 | Filipczak | |
| 4,421,128 A | 12/1983 | Boulogne et al. | |
| 4,830,673 A | 5/1989 | Jones et al. | |
| 5,168,083 A | 12/1992 | Matthews et al. | |
| 5,676,938 A | 10/1997 | Kimura et al. | |
| 5,928,658 A | 7/1999 | Kishida et al. | |
| 6,136,740 A | 10/2000 | Jones et al. | |
| 6,334,894 B1 | 1/2002 | Kostuch | |
| 6,471,762 B1 | 10/2002 | DeLuca, Jr. et al. | |
| 7,226,952 B1 | 6/2007 | Okamoto et al. | |
| 7,338,671 B2 | 3/2008 | Golz-Berner et al. | |
| 7,682,605 B2 | 3/2010 | Mateu et al. | |
| 9,084,764 B2 * | 7/2015 | Rao | A61K 45/06 |
| 2004/0191198 A1 | 9/2004 | Hochstein et al. | |
| 2005/0255077 A1 | 11/2005 | Golz-Berner et al. | |
| 2006/0013838 A1 | 1/2006 | Peng et al. | |
| 2007/0148112 A1 | 6/2007 | Dingley et al. | |
| 2008/0038475 A1 * | 2/2008 | Boschert | B41M 5/42 |
| | | | 427/420 |
| 2008/0274152 A1 | 11/2008 | Peng et al. | |
| 2009/0035333 A1 * | 2/2009 | Sasaki | A61Q 19/00 |
| | | | 514/772.3 |
| 2010/0047291 A1 | 2/2010 | Hochstein et al. | |
| 2011/0007183 A1 * | 1/2011 | Kahlman | G06T 5/70 |
| | | | 348/222.1 |
| 2012/0058165 A1 * | 3/2012 | Klofta | D06M 15/285 |
| | | | 514/782 |
| 2012/0189684 A1 | 7/2012 | Buckley et al. | |
| 2014/0050767 A1 * | 2/2014 | Rao | A61K 31/23 |
| | | | 514/552 |
| 2017/0079891 A1 * | 3/2017 | Joliff | A61Q 5/02 |
| 2018/0155517 A1 * | 6/2018 | Simancas | C08J 9/30 |

FOREIGN PATENT DOCUMENTS

| | | |
|---|---|---|
| CN | 1646614 A | 7/2005 |
| CN | 1678279 A | 7/2008 |
| CN | 103349617 A | 10/2013 |
| EP | 0 456 363 A2 | 11/1991 |
| EP | 1 106 164 A1 | 6/2001 |
| EP | 2 979 685 | 2/2016 |
| JP | 1977-012934 A | 1/1977 |
| JP | 2013-541511 A | 11/2013 |
| KR | 100 890 712 B1 | 3/2009 |
| WO | WO-95/27004 | 10/1995 |
| WO | WO 99/24360 | 5/1999 |
| WO | WO 03/091323 A1 | 11/2003 |
| WO | WO 2011/007183 A2 | 1/2011 |

OTHER PUBLICATIONS

Brazilian Search Report dated May 5, 2021, for Brazilian Application No. BR112018070188-2 (2 pgs.).
https://www.kaminllc.com/uploads/docs/TPPS/Domestic%20PDF/KaMIN%202000C.pdf.
International Search Report and Written Opinion dated Jun. 27, 2017, in International Application No. PCT/EP2017/058310 (15 pgs.).

\* cited by examiner

*Primary Examiner* — Charles I Boyer
(74) *Attorney, Agent, or Firm* — Finnegan, Henderson Farabow, Garrett & Dunner, LLP (57) ABSTRACT

The present disclosure relates to the use of kaolin as an opacifier in cosmetic compositions, cosmetic compositions comprising kaolin and methods of making said cosmetic compositions.

15 Claims, 3 Drawing Sheets

USE OF FINE PARTICLE SIZE CALCINED KAOLIN AS AN OPACIFIER IN COSMETICS

CLAIM FOR PRIORITY

This is a continuation of application Ser. No. 16/092,082, filed Oct. 8, 2018, which is a U.S. national phase entry under 35 U.S.C. § 371 from PCT International Application No. PCT/EP2017/058310, filed Apr. 6, 2017, which claims the benefit of priority of EP Application Nos. 16305412.5, filed Apr. 8, 2016, and 16306098.1, filed Aug. 31, 2016, from all of which this application claims priority and all of which are incorporated herein by reference.

TECHNICAL FIELD

The present invention generally relates to the use of kaolin as an opacifier, in particular the use of kaolin as an opacifier in cosmetic compositions. Thus, the present invention relates to a cosmetic composition comprising a cosmetically acceptable carrier and kaolin and methods of making said compositions. In particular embodiments, the cosmetic composition is a liquid cosmetic composition. In particular embodiments, the kaolin replaces some or all of another opacifier in the cosmetic composition.

BACKGROUND

Many cosmetic products are sold having a white opaque visual aspect. This is often considered to be desirable because it assists in giving consumers the impression that the product has a luxurious or smooth texture, a rich feel, a nutritious or healthy formula and/or a moisturizing effect. Many cosmetic products are initially transparent or translucent and specific chemicals (opacifiers) are added to cause the product to become white and opaque. Styrene polymers such as styrene acrylates and styrene acrylamides are examples of opacifiers typically used in cosmetic products.

It is therefore desirable to provide alternative or improved opacifiers that are suitable or intended for use in cosmetic compositions, particularly liquid cosmetic compositions. The opacifiers currently used in cosmetic products are generally artificial. Therefore, it may, for example, be desirable to provide an opacifier that is a natural product. Further, some of the opacifiers currently used in cosmetic products are not stable at particular pHs or in combination with particular substances typically present in some cosmetic products (e.g. cationic polymers). It may therefore be desirable to provide an opacifier that overcomes one or more of these problems.

SUMMARY

In accordance with a first aspect of the present invention there is provided a cosmetic composition comprising a cosmetically acceptable carrier and kaolin.

In certain embodiments, the kaolin acts as an opacifier and the cosmetic composition therefore comprises a relatively low level of (other) opacifier but has a relatively high opacity (e.g. in comparison to the opacity expected when using the relatively low level of other opacifier).

In certain embodiments, the cosmetic composition comprises less than about 0.5 wt % opacifier and has an opacity equal to or greater than about 40%. Thus, in accordance with a second aspect of the present invention there is provided a cosmetic composition comprising a cosmetically acceptable carrier, kaolin, and less than 0.5 wt % opacifier, wherein the cosmetic composition has an opacity equal to or greater than about 40%.

In certain embodiments, the cosmetic composition has an opacity that is at least about 5% greater than the opacity of the same cosmetic composition in the absence of the kaolin. Thus, in accordance with a third aspect of the present invention there is provided a cosmetic composition comprising a cosmetically acceptable carrier and kaolin, wherein the cosmetic composition has an opacity that is at least about 5% greater than the opacity of the same cosmetic composition in the absence of the kaolin.

In accordance with a fourth aspect of the present invention there is provided a use of kaolin as an opacifier in a cosmetic composition.

In certain embodiments, the kaolin is used to increase the opacity of a cosmetic composition by at least 5%. Thus, in accordance with a fifth aspect of the present invention there is provided a use of kaolin to increase the opacity of a cosmetic composition by at least 5%.

In certain embodiments, the kaolin is used to replace at least some of another opacifier in a cosmetic composition. Thus, in accordance with a sixth aspect of the present invention there is provided a use of kaolin to replace at least some of an opacifier in a cosmetic composition.

In accordance with a seventh aspect of the present invention there is provided a method of making a cosmetic composition according to any aspect or embodiment of the present invention, the method comprising combining a cosmetically acceptable carrier and kaolin.

In certain embodiments of any aspect of the present invention, the cosmetic composition has an opacity equal to or greater than about 40%. In certain embodiments, the cosmetic composition has an opacity equal to or greater than about 50% or equal to or greater than about 60%.

In certain embodiments of any aspect of the present invention, the kaolin is used as an opacifier. In certain embodiments, the kaolin is used to replace at least some of another opacifier such as a styrene opacifier, in the cosmetic composition.

In certain embodiments of any aspect of the present invention, the opacity of the cosmetic composition is at least about 5% greater than the opacity of the same cosmetic composition in the absence of kaolin. In certain embodiments, the opacity of the cosmetic composition is at least about 10% greater or at least about 20% greater than the opacity of the same cosmetic composition in the absence of kaolin. Thus, in certain embodiments, the use of kaolin in a cosmetic composition increases the opacity of the cosmetic composition by at least about 5% or at least about 10% or at least about 20%.

In certain embodiments of any aspect of the present invention, the cosmetic composition has a L* whiteness equal to or greater than about 80. In certain embodiments, the cosmetic composition has a L* whiteness equal to or greater than about 85. In certain embodiments, the cosmetic composition has a L* whiteness equal to or greater than about 90. In certain other embodiments, the cosmetic composition has a L* whiteness ranging from about 80 to about 85.

In certain embodiments of any aspect of the present invention, the cosmetic composition has a b* yellowness equal to or less than about 1. In certain embodiments, the cosmetic composition has a b* yellowness equal to or less than about 0.5 or equal to or less than about 0.

In certain embodiments of any aspect of the present invention, the cosmetic composition has a pH ranging from about 3 to about 8. In certain embodiments, the cosmetic composition has a pH ranging from about 3 to about 5 or from about 3 to about 4.

In certain embodiments of any aspect of the present invention, the cosmetic composition has a sedimentation of less than about 5% (v/v) after centrifugation at 1600 rpm for 15 minutes in a tube having a height of 10 cm and a diameter of 1.5 cm. In certain embodiments, the cosmetic composition has a sedimentation of less than about 3% (v/v) or less than about 2% (v/v) after centrifugation at 1600 rpm for 15 minutes in a tube having a height of 10 cm and a diameter of 1.5 cm In certain embodiments of any aspect of the present invention, the cosmetic composition comprises equal to or less than about 0.4 wt % opacifier. In certain embodiments, the cosmetic composition comprises equal to or less than about 0.3 wt % or equal to or less than about 0.2 wt % opacifier. In certain embodiments, the cosmetic composition is devoid of opacifier (i.e. comprises 0 wt % opacifier).

In certain embodiments of any aspect of the present invention, the kaolin is calcined kaolin.

In certain embodiments of any aspect of the present invention, the kaolin has a $d_{50}$ ranging from about 0.5 to about 0.9 µm. In certain embodiments of any aspect of the present invention, the kaolin has a $d_{90}$ ranging from about 1.8 to about 2.2 µm. In certain embodiments of any aspect of the present invention, the kaolin has a $d_{10}$ ranging from about 0.2 to about 0.6 µm.

In certain embodiments of any aspect of the present invention, the kaolin has a L* whiteness equal to or greater than about 88. In certain embodiments, the kaolin has a L* whiteness equal to or greater than about 90.

In certain embodiments of any aspect of the present invention, the kaolin has a b* yellowness equal to or less than about 3. In certain embodiments, the kaolin has a b* yellowness equal to or less than about 2.8.

In certain embodiments of any aspect of the present invention, the kaolin has a refractive index equal to or greater than about 1.2. In certain embodiments, the kaolin has a refractive index ranging from about 1.2 to about 1.8.

In certain embodiments of any aspect of the present invention, the kaolin has an oil absorption of at least about 70 g/100 g. In certain embodiments, the kaolin has an oil absorption of at least about 80 g/100 g. In certain embodiments, the kaolin has an oil absorption ranging from about 70 to about 100 g/100. In certain embodiments, the kaolin has an oil absorption ranging from about 80 to about 100 g/100 g.

In certain embodiments of any aspect of the present invention, the kaolin has a bulk density of at least about 150 g/l. In certain embodiments, the kaolin has a bulk density ranging from about 150 to about 400 g/l.

In certain embodiments of any aspect of the present invention, the kaolin has a surface area of at least about 8 m²/g. In certain embodiments, the kaolin has a surface area ranging from about 8 to about 25 m²/g.

In certain embodiments of any aspect of the present invention, the cosmetic composition is a solid or liquid cosmetic composition.

In certain embodiments of any aspect of the present invention, the cosmetic composition is a liquid soap (e.g. hand soap, body wash, hair shampoo), hair conditioner, hair styling product, sun lotion, moisturizer, deodorant or make-up composition (e.g. lipstick).

Certain embodiments of the present invention may provide one or more of the following advantages compared, for example, to opacifiers currently used in cosmetic compositions:

Environmentally friendly opacifier;
Less skin irritation and/or allergy (due to naturally, minerally-derived nature of product);
Improved stability at low and high pHs (e.g. less than pH 5.5 and more than pH 7 respectively);
Improved stability in the presence of cationic polymers (e.g. cationic conditioning agents);
Improved stability at high electrolyte concentrations;
Improved stability in the presence of ionic substances (e.g. anionic surfactants);
Whiteness, yellowness and/or opacity that is comparable to typically used opacifiers or improved;
Minimal sandy feel;
Minimal agglomeration;
Minimal change in viscosity of the cosmetic composition;
Good tolerance on skin, minimal ocular irritation;
Minimal microorganism contamination;
Advantageous effects can be obtained using amounts of kaolin that are comparable to the amount of another typical opacifier that would be used to obtain the same effect.

The details, examples and preferences provided in relation to any particular one or more of the stated aspects of the present invention apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE FIGURES

The invention may be described, without limitation, in relation to the following examples and Figures, in which.

DETAILED DESCRIPTION

Cosmetic Compositions

A cosmetic composition comprising a cosmetically acceptable carrier and kaolin is disclosed herein. It has surprisingly and advantageously been found that kaolin can be used as an opacifier in cosmetic compositions. Thus, kaolin may be used to replace opacifiers such as styrene opacifiers currently used in cosmetic compositions. In particular, it has surprisingly and advantageously been found that kaolin is stable in cosmetic compositions, in particular at low pHs and in the presence of ionic substances such as cationic conditioning agents. In particular, it has surprisingly and advantageously been found that kaolin can be used in similar quantities to currently used opacifiers to provide comparable properties such as opacity, whiteness and/or yellowness.

The cosmetic compositions may therefore comprise equal to or less than about 0.5 wt % opacifier. For example, the cosmetic compositions may comprise equal to or less than about 0.4 wt % opacifier, for example equal to or less than about 0.3 wt % opacifier, for example equal to or less than about 0.2 wt % opacifier, for example equal to or less than about 0.1 wt % opacifier. The cosmetic compositions may, for example, comprise from about 0.01 to about 0.5 wt % opacifier, for example from about 0.05 to about 0.5 wt % opacifier. The cosmetic compositions may, for example, be completely devoid of opacifier. In other words, the cosmetic compositions may comprise 0 wt % opacifier.

The term "opacifier" does not include the kaolin that is present in the cosmetic compositions disclosed herein. Thus, the term "opacifier" relates to any substance other than kaolin that is added to a material in order to increase its opacity (make more impervious to visible light). Examples of opacifiers include styrene opacifiers (any opacifier including a styrene) such as styrene acrylate copolymers and styrene acrylamide copolymers. Other examples of opacifiers include glycol stearate, glycol distearate, cetyl alcohol, cetearyl alcohol, stearyl alcohol, distearyl ether, glyceryl oleate, glyceryl stearate, acrylate polymers and copolymers, acrylamide polymers and copolymers.

The cosmetic compositions disclosed herein may, for example, have an opacity equal to or greater than about 40%. For example, the cosmetic compositions may have an opacity equal to or greater than about 45% or equal to or greater than about 50% or equal to or greater than about 55% or equal to or greater than about 60% or equal to or greater than about 65% or equal to or greater than about 70% or equal to or greater than about 75% or equal to or greater than about 80% or equal to or greater than about 85% or equal to or greater than about 90% or equal to or greater than about 95%. The cosmetic compositions may, for example, have an opacity up to about 100%, for example ranging from about 40% to about 100% or from about 40% to about 99% or from about 40% to about 98% or from about 40% to about 95%.

The cosmetic compositions disclosed herein may, for example, comprise any combination of wt % opacifier and opacity disclosed herein. For example, the cosmetic compositions disclosed herein may comprise equal to or less than about 0.5 wt % opacifier and have an opacity equal to or greater than about 40% or equal to or greater than about 50% or equal to or greater than about 60% or equal to or greater than about 70% or equal to or greater than about 80% or equal to or greater than about 90%. For example, the cosmetic compositions disclosed herein may comprise equal to or less than about 0.4 wt % opacifier and have an opacity equal to or greater than about 40% or equal to or greater than about 50% or equal to or greater than about 60% or equal to or greater than about 70% or equal to or greater than about 80% or equal to or greater than about 90%. For example, the cosmetic compositions disclosed herein may comprise equal to or less than about 0.3 wt % opacifier and have an and have an opacity equal to or greater than about 40% or equal to or greater than about 50% or equal to or greater than about 60% or equal to or greater than about 70% or equal to or greater than about 80% or equal to or greater than about 90%. For example, the cosmetic compositions disclosed herein may comprise equal to or less than about 0.2 wt % opacifier and have an opacity equal to or greater than about 40% or equal to or greater than about 50% or equal to or greater than about 60% or equal to or greater than about 70% or equal to or greater than about 80% or equal to or greater than about 90%. For example, the cosmetic compositions disclosed herein may comprise equal to or less than about 0.1 wt % opacifier and have an opacity equal to or greater than about 40% or equal to or greater than about 50% or equal to or greater than about 60% or equal to or greater than about 70% or equal to or greater than about 80% or equal to or greater than about 90%. For example, the cosmetic compositions disclosed herein may comprise 0 wt % opacifier and have an opacity equal to or greater than about 40% or equal to or greater than about 50% or equal to or greater than about 60% or equal to or greater than about 70% or equal to or greater than about 80% or equal to or greater than about 90%.

The cosmetic compositions disclosed herein may, for example, comprise any combination of wt % opacifier and opacity disclosed herein provided that the opacity of the cosmetic composition is greater than the opacity of the corresponding cosmetic composition in the absence of the kaolin. For example, the cosmetic compositions disclosed herein may have an opacity that is at least about 5% (absolute) greater than the opacity of a corresponding composition in the absence of kaolin. For example, the cosmetic composition may have an opacity that is at least about 10% greater or at least about 15% greater or at least about 20% greater or at least about 25% greater or at least about 30% greater or at least about 35% greater or at least about 40% greater or at least about 45% greater or at least about 50% greater or at least about 55% greater or at least about 60% greater or at least about 65% greater or at least about 70% greater or at least about 75% greater or at least about 80% greater than the opacity of the corresponding cosmetic composition in the absence of the kaolin. The "corresponding cosmetic composition in the absence of kaolin" refers to a cosmetic composition that is identical to the subject cosmetic composition except that it does not comprise the kaolin.

The cosmetic compositions may, for example, have an opacity that is within (+/−) 10% of the opacity of a corresponding cosmetic composition comprising Opulyn™ 301 in place of the kaolin (e.g. where opacity of cosmetic composition comprising Opulyn™ 301 is 80%, the opacity of the subject cosmetic composition ranges from 70% to 90%). For example, the cosmetic composition may have an opacity that is within 9% or 8% or 7% or 6% or 5% or 4% or 3% or 2% of the opacity of a corresponding cosmetic composition comprising Opulyn™ 301 in place of the kaolin.

Opacity of the cosmetic compositions is measured using the contrast card method. A transparent container that is 1 cm high and 3.5 cm diameter containing the cosmetic composition is placed on a black/white contrast card. A spectrophotometer is used to determine the whiteness of the film on the black surface ($Y_{black}$) and the whiteness of the film on the white ($Y_{white}$) surface. Opacity (%)=($Y_{black}$/$Y_{white}$)×100. Opacity is measured using Colorimeter BYK Sprtro guide 44/0 guide gloss.

The cosmetic compositions may, for example, have a L* whiteness of at least about 80. For example, the cosmetic compositions may have a L* whiteness equal to or greater than about 82 or equal to or greater than about 84 equal to or greater than about 85 or equal to or greater than about 86 or equal to or greater than about 88 or equal to or greater than about 90 or equal to or greater than about 92 or equal to or greater than about 94 or equal to or greater than about 95. The cosmetic compositions may, for example, have a L* whiteness up to about 100 or up to about 99 or up to about 98 or up to about 97 or up to about 96. The cosmetic compositions may, for example, have a L* whiteness ranging from about 80 to about 90 or from about 80 to about 85.

The cosmetic compositions may, for example, have a b* yellowness equal to or less than about 1. For example, the cosmetic compositions may have a b* yellowness equal to or less than about 0.9 or equal to or less than about 0.8 or equal to or less than about 0.7 or equal to or less than about 0.6 or equal to or less than about 0.5 or equal to or less than about 0.4 or equal to or less than about 0.3 or equal to or less than about 0.2 or equal to or less than about 0.1 or equal to or less than about 0 or equal to or less than about −0.1 or equal to or less than about −0.2 or equal to or less than about −0.3 or equal to or less than about −0.4 or equal to or less than about −0.5. The cosmetic compositions may, for example, have a b* yellowness equal to or greater than about −100 or equal to or greater than about −50 or equal to or greater than about −25 or equal to or greater than about −20 or equal to or greater than about −10 or equal to or greater than about −5 or equal to or greater than about −4.

The L* whiteness and b* yellowness are determined using the L*a*b* colour space. L* whiteness and b* yellowness of the cosmetic composition may be measured using the spectrophotometer MINOLTA CM-3700d (illuminant D65/10°). In this method, the cosmetic composition is contained in a 1 cm high transparent container having a diameter of 3.5 cm.

The cosmetic compositions disclosed herein may have a pH ranging from about 3 to about 8. For example, the cosmetic compositions disclosed herein may have a pH ranging from about 3.5 to about 7.5 or from about 4 to about 7 or from about 4.5 to about 6.5 or from about 5 to about 6. For example, the cosmetic compositions may have a pH ranging from about 3 to about 5.5 or from about 3 to about 5 or from about 3 to about 4.5 or from about 3 to about 4. For example, the cosmetic compositions may have a pH ranging from about 7 to about 8.

The cosmetic compositions disclosed herein may be stable and therefore may experience no or only minimal flocculation and/or sedimentation and/or creaming. In particular, the cosmetic compositions may exhibit no or only minimal flocculation and/or sedimentation and/or creaming when it has a pH ranging from about 3 to about 8 or from about 3 to about 6 or from about 3 to about 5 or from about 3 to about 4. In particular, the cosmetic compositions may exhibit no or only minimal flocculation and/or sedimentation and/or creaming when in the presence of cationic polymers such as cationic conditioning agents.

For example, equal to or less than about 5% (v/v) sedimentation of the cosmetic composition may occur after centrifugation at 1600 rpm for 15 minutes in a tube having a height of 10 cm and a diameter of 1.5 cm. For example, equal to or less than about 4% (v/v) or equal to or less than about 3% (v/v) or equal to or less than about 2% (v/v) or equal to or less than about 1% (v/v) or equal to or less than about 0.5% (v/v) sedimentation of the cosmetic composition may occur after centrifugation at 1600 rpm for 15 minutes in a tube having a height of 10 cm and a diameter of 1.5 cm. For example no sedimentation of the cosmetic composition may occur after centrifugation at 1600 rpm for 15 minutes using in a tube having a height of 10 cm and a diameter of 1.5 cm. In particular, the cosmetic compositions may exhibit sedimentation within this range when it has a pH ranging from about 3 to about 8 or from about 3 to about 6 or from about 3 to about 5 or from about 3 to about 4. In particular, the cosmetic compositions may exhibit sedimentation within this range when in the presence of cationic polymers such as cationic conditioning agents.

Stability (flocculation and/or sedimentation and/or creaming) may be determined by measuring the change in backscattering over time. Backscattering of a cosmetic composition using a Turbiscan® sensor can be measured at different points in time. Changes in backscattering indicate a change in stability (e.g. flocculation and/or sedimentation and/or creaming).

The light backscattered by the cosmetic composition may, for example, change by no more than about 20% (+ or −20%) over, for example, 1 day, 2 days, 3 days, 7 days, 14 days, 21 days, 28 days, 2 months, 3 months, 4 months, 5 months, 6 months, 1 year or 2 years). For example, the light backscattered by the cosmetic composition may change by no more than about 15% or no more than about 10% or no more than about 5% over, for example, 1 day, 2 days, 3 days, 7 days, 14 days, 21 days, 28 days, 2 months, 3 months, 4 months, 5 months, 6 months, 1 year or 2 years).

The kaolin may, for example, be hydrous kaolin or calcined kaolin (partially or fully calcined kaolin) or metakaolin.

To form the metakaolin or calcined kaolin, the calcination temperature may be controlled so that the kaolin undergoes a characteristic endothermic dehydration reaction, and the original minerals (e.g. kaolinite) may be fully or partially dehydroxylated. Calcination temperature may be held significantly below that at which the metakaolin collapses, as would be indicated by a sharp exotherm in the differential thermal analysis (DTA). In contrast, fully calcined kaolin pigments may be calcined at temperatures above this exotherm.

The kaolin may, for example, undergo dehydroxylation by calcination. This is a thermal treatment process, generally in the presence of air or oxygen. Calcination changes the kaolin structure from crystalline to amorphous. The degree to which kaolin undergoes changes in crystalline form may depend on the amount of heat to which it is subjected. Generally, the higher the temperature, the shorter the calcination time. Generally, calcination is performed at temperatures ranging from about 550° C. to about 950° C. (for example from about 750° C. to about 950° C., for example from about 850° C. to about 900° C.) to produce the calcined kaolin or metakaolin. Further heating to temperatures around about 900 to 950° C. may result in further structural changes such as densification and formation of an aluminium-silicon spinel ($Si_3Al_4O_{12}$). At approximately 950° C., amorphous regions of kaolin (e.g. metakaolin) may begin to re-crystallize. Further heating to temperatures around about 1050° C. and above may result in further structural changes to form mullite $3Al_2O_3 \cdot 2SiO_2$ and highly crystalline cristobalite $SiO_2$.

For example, any furnace, kiln or other suitable heating apparatus may be used for the calcination of the kaolin. A typical procedure involves heating kaolin in a kiln, for example a conventional rotary kiln. Typically, the kaolin may be introduced into the kiln as an extrudate from a pug mill. As the kaolin proceeds through the kiln, typically at a starting moisture content of about 25% by weight to facilitate the extrusion of the first kaolin, the extrudate breaks down into pellets as a result of the calcination process. A small amount of binder (such as alum) may be added to the kaolin) to provide "green strength" to the kaolin so as to prevent the kaolin from completely breaking down into powder form during the calcination process.

The calcination process used may, for example, be soak calcining, i.e. wherein the kaolin or clay is calcined for a period of time during which the chemistry of the material is gradually changed by the effect of heating. The calcining may for example be for a period of at least 1 minute, in many cases at least 10 minutes, e.g. from 30 minutes to five or more hours. Known devices suitable for carrying out soak calcining include high temperature ovens, rotary kilns and vertical kilns.

The calcination process may, for example, be flash calcining, wherein the hydrous kaolin is typically rapidly heated over a period of less than one second, e.g. less than 0.5 seconds. Flash calcination may, for example, introduce kaolin (e.g. water washed kaolin) to a hot gas stream for a few seconds. Flash calcination refers to heating a material at an extremely fast rate, almost instantaneously. The heating rate in a flash calciner may be of the order of 56,000° C. per second or greater, such as about 100,000° C. to about 200,000° C. per second. The kaolin may, for example, be prepared by flash calcination, wherein the clay may be exposed to a temperature greater than 500° C. for a time not more than 5 seconds. The kaolin may, for example, be calcined to a temperature in the range of from 550° C. to 1200° C.; for microsecond periods the temperature may be as high as 1500° C. The kaolin may be calcined to a temperature in the range of from 800° C. to 1100° C.; for example a temperature in the range of from 900° C. to 1050° C.; for example a temperature in the range of from 950° C. to 1000° C. The kaolin may, for example, be calcined for a time less than 5 seconds; for example for less than 1 second; for example for less than 0.5 seconds; for example for less than 0.1 seconds. Flash calcination of kaolin particles gives rise to relatively rapid blistering of the particles caused by relatively rapid dehydroxylation of the kaolin. Water vapour is generated during calcination which may expand extremely rapidly, in fact generally faster than the water vapour can diffuse through the crystal structure of the particles. The pressures generated are sufficient to produce sealed voids as the interlayer hydroxyl groups are driven off, and it is the swollen interlayer spaces, voids, or blisters between the kaolin platelets which typify flash calcined kaolins and give them characteristic properties.

The flash calcination process may, for example, be carried out by injecting the kaolin into a combustion chamber or furnace wherein a vortex may be established to rapidly remove the calcined kaolin from the combustion chamber. A suitable furnace would be one in which a toroidal fluid flow heating zone is established such as the device described in WO 99/24360 and corresponding applications U.S. Pat. Nos. 6,334,894 and 6,136,740, the contents of which are herein incorporated by reference in their entirety.

The kaolin may, for example, undergo one or more sizing and/or comminution steps prior to or after any optional dehydroxylation. For example, the kaolin may undergo comminution by crushing or grinding or milling. For example, the kaolin may undergo sizing using screens, centrifuges, cyclones and air classifiers. Screening can be performed using screens of a desired mesh, such as a 325 mesh screen. Other methods include gravity sedimentation or elutriation, any type of hydrocyclone apparatus, or, for example, a solid bowl decanter centrifuge, and disc nozzle centrifuge. The resultant coarse fraction may be discarded, used as a separate product or, for example, may be redirected back to the comminution tank. The kaolin may, for example, undergo densification or concentration steps, for example by gravity concentration, froth flotation and/or dewatering.

The kaolin may, for example, have a $d_{50}$ ranging from about 0.5 μm to about 0.9 μm. For example, the kaolin may have a $d_{50}$ ranging from about 0.55 μm to about 0.85 μm or from about 0.6 μm to about 0.8 μm or from about 0.65 μm to about 0.75 μm or from about 0.6 μm to about 0.7 μm. The kaolin, may, for example, have a $d_{50}$ ranging from about 0.6 μm to about 0.8 μm or from about 0.65 μm to about 0.75 μm. For example, the kaolin may have a $d_{50}$ of about 0.7 μm.

The kaolin may, for example, have a $d_{90}$ ranging from about 1.8 μm to about 2.2 μm. For example, the kaolin may have a $d_{90}$ ranging from about 1.85 μm to about 2.15 μm or from about 1.9 μm to about 2.1 μm or from about 1.95 μm to about 2.05 μm or from about 2 μm to about 2.1 μm. The kaolin, may, for example, have a $d_{90}$ ranging from about 1.9 μm to about 2.1 μm or from about 1.95 μm to about 2.05 μm. For example, the kaolin may have a $d_{90}$ of about 2 μm.

The kaolin may, for example, have a $d_{10}$ ranging from about 0.2 μm to about 0.6 μm. For example, the kaolin may have a $d_{10}$ ranging from about 0.25 μm to about 0.55 μm or from about 0.3 μm to about 0.5 μm or from about 0.35 μm to about 0.45 μm or from about 0.4 μm to about 0.5 μm. The kaolin, may, for example, have a $d_{10}$ ranging from about 0.3 μm to about 0.5 μm or from about 0.35 μm to about 0.45 μm. For example, the kaolin may have a $d_{50}$ of about 0.4 μm.

The kaolin may, for example, have a $d_{50}$ ranging from about 0.6 to about 0.8 μm and a $d_{90}$ ranging from about 1.9 to about 2.1 μm. The kaolin may, for example, have a $d_{50}$ ranging from about 0.6 to about 0.8 μm and a $d_{90}$ ranging from about 1.9 to about 2.1 μm and a $d_{10}$ ranging from about 0.3 to about 0.5 μm.

Unless otherwise stated, the particle sizes and other particle size properties referred to herein are measured in a well-known manner by sedimentation of the particulate material in a fully dispersed condition in an aqueous medium using a SediGraph III 5120 instrument as supplied by Micrometrics Corporation Norcross, Georgia, USA (telephone: +17706623620; web-site: www.micromeritics.com), referred to herein as a "Micromeritics Sedigraph 5120 unit" (standard method ISO 13317-3). Such a machine provides measurements and a plot of the cumulative percentage by weight of particles having a size, referred to in the art as the 'equivalent spherical diameter' (e.s.d), less than given e.s.d values. The mean particle size, or the $d_{50}$ value, is the value determined in this way of the particle e.s.d. at which there are 50% by weight of the particles which have an equivalent spherical diameter less than that $d_{50}$ value. The $d_{90}$ and $d_{10}$ are the values determined in this way of the particle e.s.d. at which there are 90% and 10% respectively by weight of the particles which have an equivalent spherical diameter less than that $d_{90}$ or $d_{10}$ value.

The kaolin may, for example, have a L* whiteness equal to or greater than about 88. For example, the kaolin may have a L* whiteness equal to or greater than about 90 or equal to or greater than about 92 or equal to or greater than about 94 or equal to or greater than about 95 or equal to or greater than about 96 or equal to or greater than about 97. The kaolin may, for example, have a L* whiteness of about 97, for example about 97.5. The kaolin may, for example, have a L* whiteness up to about 100. The kaolin may, for example, have a L* whiteness up to about 99 or up to about 98.

The kaolin may, for example, have a b* yellowness equal to or less than about 3. For example, the kaolin may have a b* yellowness equal to or less than about 2.9 or equal to or less than about 2.8 or equal to or less than about 2.7. The kaolin may, for example, have a b* yellowness of about 2.6. The kaolin may, for example, have a b* yellowness equal to or greater than about −100. For example, the kaolin may have a b* yellowness equal to or greater than about −50 or equal to or greater than about −25 or equal to or greater than about −20 or equal to or greater than about −10 or equal to or greater than about −5 or equal to or greater than about −4.

The kaolin may, for example, have an a* greenness equal to or less than about 0. For example, the kaolin may have an a* greenness equal to or less than about −0.05 or equal to or less than about −0.06 or equal to or less than about −0.07 or equal to or less than about −0.08 or equal to or less than about −0.09 or equal to or less than about −0.1. For example, the kaolin may have an a* greenness equal to or greater than about −1 or equal to or greater than about −0.5 or equal to or greater than about −0.4 or equal to or greater than about −0.3 or equal to or greater than about −0.2.

The L* whiteness, a* greenness and b* yellowness are determined using the L*a*b* colour space. L* whiteness, a* greenness and b* yellowness of the cosmetic composition may be measured using the spectrophotometer MINOLTA CM-3700d as described above for the cosmetic compositions.

The kaolin may, for example, have a refractive index of at least about 1.2. For example, the kaolin may have a refractive index of at least about 1.3 or at least about 1.4 or at least about 1.5. For example, the kaolin may have a refractive index of about 1.5, for example about 1.55. The kaolin may, for example, have a refractive index up to about 2. For example, the kaolin may have a refractive index up to about 1.9 or up to about 1.8 or up to about 1.7 or up to about 1.6.

The refractive index of the kaolin is measured using a refractometer (model Bellingham & Stanley Ltd London No. 9200077) that has been calibrated using compositions comprising different ratios of ethylene glycol and water.

The kaolin may, for example, have an oil absorption of at least about 70 g/100 g. For example, the kaolin may have an oil absorption of at least about 72 or at least about 74 or at least about 75 or at least about 78 or at least about 80 g/100 g. For example, the kaolin may have an oil absorption of at least about 81 or at least about 82 or at least about 83 or at least about 84 g/100 g. For example, the kaolin may have an oil absorption of about 84 g/100 g. The kaolin may, for example, have an oil absorption up to about 100 g/100 g. For example, the kaolin may have an oil absorption up to about 95 g/100 g or up to about 90 g/100 g or up to about 85 g/100 g.

The oil absorption of the kaolin is the quantity of oil (test with linseed) added to 4 g of mineral to obtain a stiff, smooth paste. The oil absorption value (mL/100 g) evaluates a mineral's capacity to absorb the oil and organic components (standard method IS 787/5).

The kaolin may, for example, have a bulk density of at least about 150 g/l. For example, the kaolin may have a bulk density of at least about 160 g/l or at least about 170 g/l or at least about 180 g/l or at least about 190 g/l or at least about 195 g/l. For example, the kaolin may have a bulk density of about 200 g/l. The kaolin may, for example, have a bulk density up to about 400 g/l. For example, the kaolin may have a bulk density up to about 350 g/l or up to about 300 g/l or up to about 290 g/l or up to about 280 g/l or up to about 270 g/l or up to about 260 g/l or up to about 250 g/l or up to about 240 g/l or up to about 230 g/l or up to about 220 g/l or up to about 210 g/l.

The bulk density of the kaolin is measured by putting the kaolin in a container with a known volume and weighing it (standard method EN 1097/3).

The kaolin may, for example, have a surface area of at least about 8 $m^2/g$. For example, the kaolin may have a surface area of at least about 9 $m^2/g$ or at least about 10 $m^2/g$ or at least about 11 $m^2/g$ or at least about 12 $m^2/g$ or at least about 13 $m^2/g$. For example, the kaolin may have a surface area of about 14 $m^2/g$. The kaolin may, for example, have a surface area up to about 25 $m^2/g$. For example, the kaolin may have a surface area up to about 20 $m^2/g$ or up to about 19 $m^2/g$ or up to about 18 $m^2/g$ or up to about 17 $m^2/g$ or up to about 16 $m^2/g$ or up to about 15 $m^2/g$.

The surface area of the kaolin may be measured by BET nitrogen absorption according to DIN ISO 9277, for example using a TriStar machine, available from Micromeritics.

The kaolin may, for example, have a specific gravity of at least about 2. For example, the kaolin may have a specific gravity of at least about 2.1 or at least about 2.2 or at least about 2.3 or at least about 2.4 or at least about 2.5 or at least about 2.6. For example, the kaolin may have a specific gravity up to about 3 or up to about 2.9 or up to about 2.8 or up to about 2.7.

The specific gravity of the kaolin is measured by calculating the mass of a dried powder divided by its volume, which is calculated using water as the displacing medium at room temperature.

The kaolin may, for example, be present in the cosmetic composition in an amount ranging from about 0.1 wt % to about 5 wt %. For example, the kaolin may be present in the cosmetic composition in an amount ranging from about 0.1 wt % to about 4 wt % or from about 0.1 wt % to about 3 wt % or from about 0.1 wt % to about 2 wt %. For example, the kaolin may be present in the cosmetic composition in an amount ranging from about 0.1 wt % to about 1.9 wt % or from about 0.1 wt % to about 1.8 wt % or from about 0.1 wt % to about 1.7 wt % or from about 0.1 wt % to about 1.6 wt % or from about 0.1 wt % to about 1.5 wt % or from about 0.1 wt % to about 1.4 wt % or from about 0.1 wt % to about 1.3 wt % or from about 0.1 wt % to about 1.2 wt % or from about 0.1 wt % to about 1.1 wt % or from about 0.1 wt % to about 1 wt %. For example, the kaolin may be present in the cosmetic composition in an amount ranging from about 0.1 wt % to about 0.9 wt % or from about 0.2 wt % to about 0.8 wt % or from about 0.3 wt % to about 0.7 wt %.

The cosmetic composition may, for example, be a liquid cosmetic composition. The cosmetic composition may, for example, be a liquid soap, a hair conditioner, a hair styling product, a sun lotion, a moisturizer, a deodorant or a liquid make-up composition. The liquid soap may, for example, be a hand soap and/or body wash and/or hair shampoo.

The cosmetic composition may, for example, be a solid cosmetic composition. The cosmetic composition may, for example, be a solid hair-styling product, a solid deodorant or solid make-up composition. For example, the cosmetic composition may be lipstick.

The cosmetically acceptable carrier is a medium that is compatible with application to any keratinous surface (e.g. skin, lips or hair) of a living being (e.g. human). Consequently, cosmetic compositions according to the present disclosure may be free of compounds that are incompatible with and/or not tolerated for application to the skin, lips and/or hair. The term "compatible" may, for example, mean that the carrier does not cause irritation of the keratinous surface to which it is applied.

Suitable cosmetically acceptable carriers will be known to those skilled in the art and will be selected according to the intended end-use of the cosmetic composition. The cosmetically acceptable carrier may be in a variety of forms including as a solution, a colloidal dispersion, an oil-in-water emulsion, a water-in-oil emulsion, a suspension, a cream, a lotion, a gel, a foam, a mousse, a spray or a solid.

For example, a cosmetic composition (e.g. make-up or lipstick composition) may comprise a cosmetically acceptable carrier comprising one or more oils (e.g. one or more vegetable oils (e.g. castor oil) and/or one or more mineral oils) and/or one or more waxes (e.g. one or more vegetable waxes and/or one or more mineral waxes and/or one or more synthetic waxes) and/or one or more fatty alcohols and/or one or more fatty acid esters.

The cosmetic composition may comprise one or more standard cosmetic ingredients, such as, for example, pigments (e.g. colour pigments and/or $TiO_2$), absorbent powders, perfumes, hydrophilic or lipophilic gelling and/or thickening agents, anti-settling agents, antioxidants, fragrances, preservatives, neutralizing agents, sunscreen agents (e.g. UV filters), vitamins, moisturizing agents, conditioning agents, self-tanning compounds, anti-wrinkle actives, emollients, hydrophilic or lipophilic active principles, agents for combating free radicals, sequestering agents, colouring agents, pearlescent agents and film-forming agents. The cosmetic ingredients included in the cosmetic composition may be chosen according to the intended end-use of the cosmetic composition. The cosmetic ingredients may also be "cosmetically acceptable" in that they are compatible with application to any keratinous surface (e.g. skin, lips or hair) of a living being (e.g. human).

The cosmetically acceptable carrier and any standard cosmetic ingredients may, for example, make-up up to 99.9 wt % of the cosmetic composition. For example, the cosmetically acceptable carrier and standard cosmetic ingredients may make-up up to 99 wt % of the cosmetic composition or up to about 98.5 wt % or up to about 98 wt % or up to about 97.5 wt % or up to about 97 wt % of the cosmetic composition.

For example, a lipstick composition may comprise up to about 99 wt % of a cosmetically acceptable carrier, from about 1 wt % to about 10 wt % of pigments and from about 0.5 wt % to about 3 wt % of standard cosmetic ingredients.

Uses

The use of kaolin as an opacifier in a cosmetic composition is also disclosed herein. The cosmetic composition and kaolin may, for example, be according to any of the embodiments described above, including any combination thereof.

The kaolin may, for example, be used to replace at least some of one or more opacifiers in a cosmetic composition. For example, the kaolin may be used to replace at least about 20 wt % of the opacifier(s) in a cosmetic composition or at least about 30 wt % or at least about 40 wt % or at least about 50 wt % or at least about 60 wt % or at least about 70 wt % or at least about 80 wt % or at least about 90 wt % or at least about 95 wt % of the opacifier(s) in a cosmetic composition. For example, the kaolin may be used to replace all of the opacifier(s) in a cosmetic composition.

The kaolin may, for example, be used to replace one or more opacifiers in a cosmetic composition at a ratio from 1 wt % opacifier:1 wt % kaolin to 1 wt % opacifier:1.5 wt % kaolin.

Replacing at least some of one or more opacifiers in a cosmetic composition may, for example, change the absolute opacity of the cosmetic composition by no more than about 10% (i.e. +1-10%). For example, replacing at least some of one or more opacifiers in a cosmetic composition may change the opacity of the cosmetic composition by no more than about 9% or no more than about 8% or no more than about 7% or no more than about 6% or no more than about 5% or no more than about 4% or no more than about 3% or no more than about 2% or no more than about 1%.

The kaolin may, for example, be used to increase the opacity of a cosmetic composition by at least about 5%. For example, the kaolin may be used to increase the opacity of a cosmetic composition by at least about 10% or at least about 15% or at least about 20% or at least about 25% or at least about 30% or at least about 35% or at least about 40% or at least about 45% or at least about 50% or at least about 55% or at least about 60% or at least about 65% or at least about 70% or at least about 75% or at least about 80%. The kaolin may, for example, be used to increase the opacity of a cosmetic composition when the cosmetic composition comprises equal to or less than about 0.5 wt % opacifier or equal to or less than about 0.4 wt % opacifier or equal to or less than about 0.3 wt % opacifier or equal to or less than about 0.2 wt % opacifier or equal to or less than about 0.1 wt % opacifier. The kaolin may, for example, be used to increase the opacity of a cosmetic composition when the cosmetic composition comprises 0 wt % opacifier.

Methods of Making Cosmetic Compositions

Methods of making the cosmetic composition disclosed herein are also disclosed herein. The methods comprise combining a cosmetically acceptable carrier and kaolin and any other optional ingredients. The components of the cosmetic composition may, for example, be mixed, using apparatus known to those skilled in the art, to form, for example, a solution, a colloidal dispersion, an oil-in-water emulsion, a water-in-oil emulsion, a suspension, a cream, a lotion, a gel, a foam, a mousse or a spray.

EXAMPLES

Example 1

Compositions comprising 2 wt % of mineral in Sanex® Zero % shower gel were made using the minerals shown in Table 1. A composition comprising 1 wt % Opulyn™ 301 (Styrene/Acrylate copolymer having an average particle size of 0.17 mm, density of 1.03 G/MI and viscosity of 50 Cps) in Sanex® Zero % shower gel was also made as a control.

Figure 1:
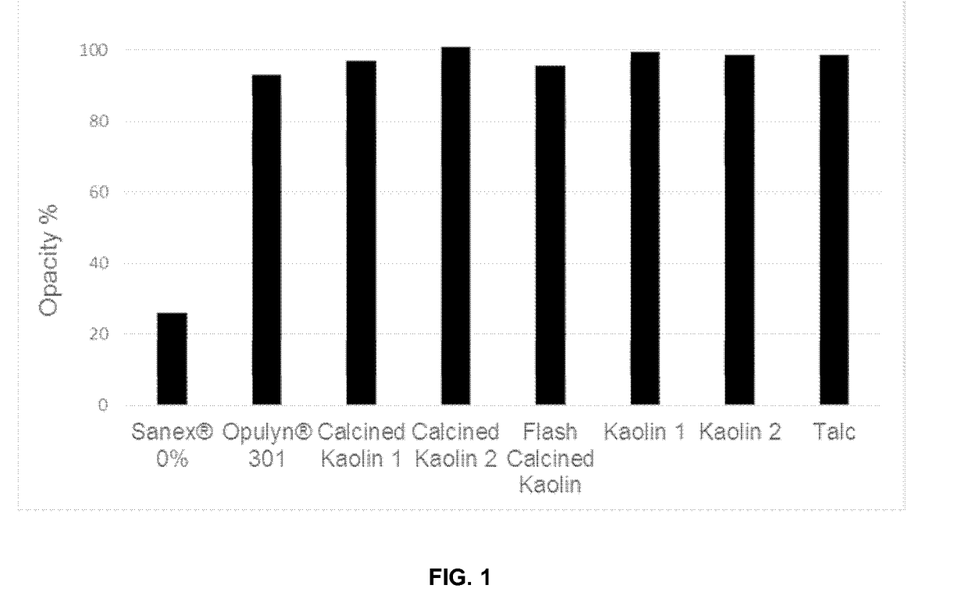
FIG. 1 shows the opacity of the various compositions prepared in Example 1.

The opacity of the compositions was determined using the contrast card method described above using a transparent container having a height of 1 cm and diameter of 3.5 cm. The results are shown in FIG. 1.

Figure 2:
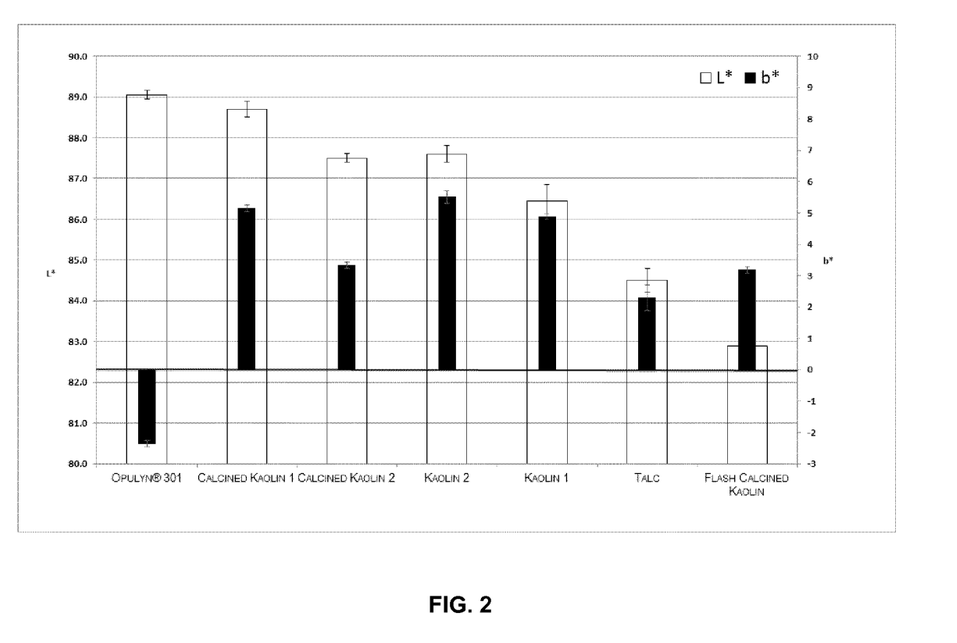
FIG. 2 shows the L* whiteness and b* yellowness of the various compositions prepared in Example 1.

The L* whiteness and b* yellowness of the compositions was determined as described above. The results are shown in FIG. 2.

Figure 3:
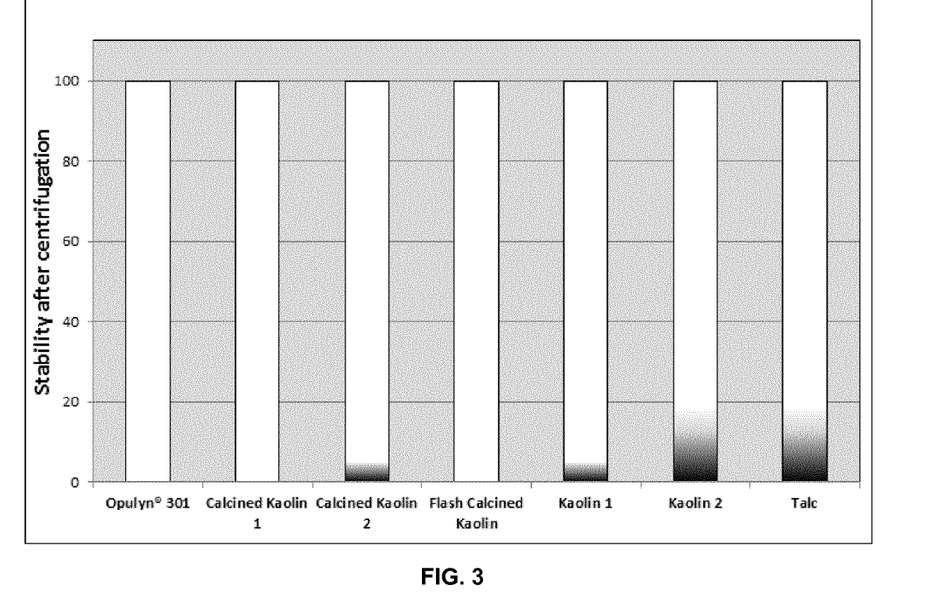
FIG. 3 shows the sedimentation of the various compositions prepared in Example 1.

The stability of the compositions after centrifugation at 1600 rpm for 15 minutes in a tube having a height of 10 cm and a diameter of 1.5 cm was also determined. The results are shown in FIG. 3.

Example 2

Compositions comprising 0.75 wt % of mineral in Sanex® Zero % shower gel were made using the minerals shown in Table 2. A composition comprising 0.5 wt % Opulyn™ 301 (Styrene/Acrylate copolymer having an average particle size of 0.17 mm, density of 1.03 G/MI and viscosity of 50 Cps) in Sanex® Zero % shower gel was also made as a control.

Figure 4:
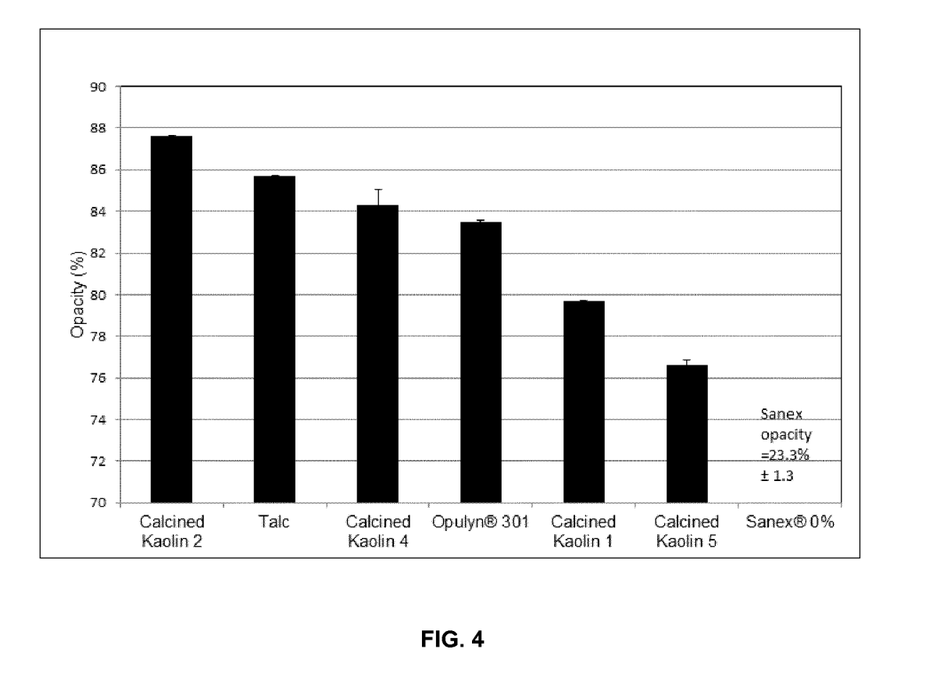
FIG. 4 shows the opacity of the various compositions prepared in Example 2.

The opacity of the compositions was determined using the contrast card method described above. The results are shown in FIG. 4.

Figure 5:
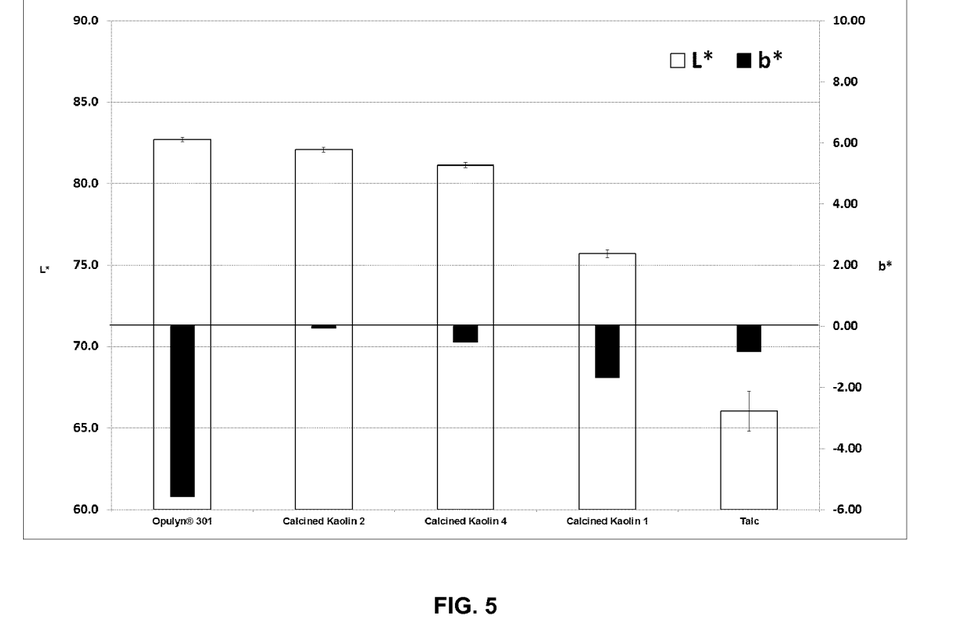
FIG. 5 shows the L* whiteness and b* yellowness of the various compositions prepared in Example 2.

The L* whiteness and b* yellowness of the compositions was determined as described above. The results are shown in FIG. 5.

Figure 6:
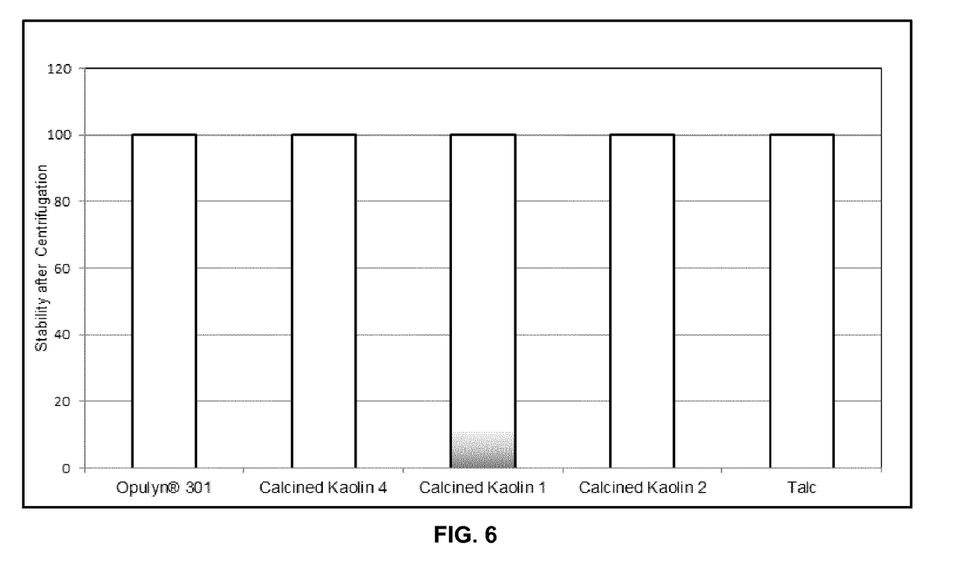
FIG. 6 shows the sedimentation of the various compositions prepared in Example 2.

The stability of the compositions after centrifugation at 1600 rpm for 15 minutes in a tube having a height of 10 cm and a diameter of 1.5 cm was also determined. The results are shown in FIG. 6.

TABLE 1

| Product type | YEL | L* | a* | b* | $d_{10}$ (μm) | $d_{50}$ (μm) | $d_{90}$ (μm) | Oil Absorption (g/100 g) | Specific Gravity | Bulk density (g/l) | Surface area (BET $m^2/g$) | Refractive Index |
|---|---|---|---|---|---|---|---|---|---|---|---|---|
| Talc | — | 96.9 | −0.06 | 0.81 | 0.28 | 0.5 | 1.5 | 72 | 2.78 | 90 | 22.9 | 1.33 |
| Kaolin 1 | 4.3 | 96.9 | −0.12 | 2.8 | — | 0.18 | 0.3 | 48 | 2.6 | 280 | 29 | 1.55 |
| Kaolin 2 | 4.6 | 96.9 | −0.18 | 3.0 | — | 0.2 | 0.5 | 40 | 2.6 | 260 | 19 | 1.55 |
| Calcined kaolin 1 | 3.9 | 97.5 | −0.11 | 2.6 | 0.4 | 0.7 | 2.0 | 84 | 2.62 | 200 | 14 | 1.55 |
| Calcined kaolin 2 | 3.4 | 97.4 | −0.28 | 2.34 | 0.5 | 1.1 | 5.5 | 56 | 2.63 | 362 | 10.6 | 1.62 |
| Flash calcined kaolin | 3.8 | 96.5 | −0.19 | 2.5 | 0.8 | 2 | 6.0 | 65 | 2.3 | 260 | 11 | 1.55 |

TABLE 2

| Product type | YEL | L* | a* | b* | $d_{10}$ (μm) | $d_{50}$ (μm) | $d_{90}$ (μm) | Oil Absorption (g/100 g) | Specific Gravity | Bulk density (g/l) | Surface area (BET $m^2/g$) | Refractive Index |
|---|---|---|---|---|---|---|---|---|---|---|---|---|
| Talc | — | 97.75 | 0.14 | 0.25 | 0.72 | 1.3 | 3.2 | — | 2.78 | — | 12.3 | 1.33 |
| Calcined kaolin 1 | 4.6 | 97.8 | 0.02 | 2.9 | 0.8 | 1.8 | 4.7 | 51 | 2.55 | 230.0 | 8 | 1.55 |
| Calcined kaolin 2 | 3.9 | 97.5 | −0.11 | 2.6 | 0.4 | 0.7 | 2.0 | 84 | 2.62 | 200 | 14 | 1.55 |
| Calcined kaolin 3 | 3.4 | 97.4 | −0.28 | 2.34 | 0.5 | 1.1 | 5.5 | 56 | 2.63 | 362 | 10.6 | 1.62 |
| Calcined kaolin 4 | 3.4 | 97.5 | −0.14 | 2.26 | 0.4 | 0.7 | 1.9 | 104 | 2.62 | 180 | 15 | 1.62 |
| Calcined kaolin 5 | 0.8 | 96.8 | 0.02 | 0.51 | 2 | 3.5 | 8 | 93 | 2.6 | — | — | 1.55 |

Example 3

The viscosity of the compositions described in Example 2 was determined using a Brookfield machine, mobile 4 after mixing for 1 minute at 1, 10 and 100 rpm. The results are shown in Table 3.

TABLE 3

| Sample | Viscosity after 1 rpm (Poise) | Viscosity after 10 rpm (Poise) | Viscosity after 100 rpm (Poise) | pH |
|---|---|---|---|---|
| Sanex ® 0% + water | 105 | 104 | 31.3 | 4.59 |
| Sanex ® 0% + 0.5 wt % Opulyn ™ 301 | 54 | 49.2 | 22.2 | 5.9* |
| Sanex ® 0% + 0.75 wt % kaolin 4 | 118 | 108 | 30.2 | 4.54 |
| Sanex ® 0% + 0.75 wt % kaolin 1 | 108 | 104 | 30.6 | 4.57 |
| Sanex ® 0% + 0.75 wt % kaolin 2 | 116 | 114 | 32.4 | 4.58 |
| Sanex ® 0% + 0.75 wt % Talc | 108 | 106 | 31.4 | 4.66 |
| Sanex ® 0% + 0.75 wt % kaolin 5 | 128 | 121 | 30.3 | 4.59 |

*The pH of the composition comprising Opulyn ™ 310 was regulated with a base according to the manufacturer's instructions (Opulyn ™ 301 can be used from pH 5.5).

The minerals had minimal impact on viscosity and pH. This means that it is not necessary to change the formulations of current cosmetic compositions on the market.

The invention claimed is:

1. A cosmetic composition comprising:
   a cosmetically acceptable carrier;
   calcined kaolin having an oil absorption of at least about 70 g/100 g, a $d_{10}$ ranging from about 0.2 to about 0.6 μm, a $d_{50}$ ranging from 0.5 to 0.9 μm, and a $d_{90}$ ranging from about 1.8 to about 2.2 μm; and
   optionally less than about 0.5 wt % of an opacifier;
   wherein the cosmetic composition has an opacity equal to or greater than about 40%;
   wherein the cosmetic composition is a liquid soap, hair conditioner, hair styling product, sun lotion, moisturizer, deodorant, or make-up composition.

2. The cosmetic composition of claim 1, wherein the cosmetic composition has an opacity equal to or greater than about 50%.

3. The cosmetic composition of claim 1, wherein the cosmetic composition has a L* whiteness equal to or greater than about 80.

4. The cosmetic composition of claim 1, wherein the cosmetic composition has a b* yellowness equal to or less than about 1.

5. The cosmetic composition of claim 1, wherein the cosmetic composition has a pH ranging from about 3 to about 8.

6. The cosmetic composition of claim 1, wherein the cosmetic composition has a sedimentation of less than 5% (v/v) after centrifugation at 1600 rpm for 15 minutes in a tube having a height of 10 cm and a diameter of 1.5 cm.

7. The cosmetic composition of claim 1, wherein the cosmetic composition comprises equal to or less than about 0.4 wt % of an opacifier.

8. The cosmetic composition of claim 1, wherein the cosmetic composition comprises 0 wt % of an opacifier.

9. The cosmetic composition of claim 1, wherein the kaolin has a L* whiteness of at least about 88.

10. The cosmetic composition of claim 9, wherein the kaolin has a b* yellowness equal to or less than about 3.

11. The cosmetic composition of claim 1, wherein the kaolin has a refractive index of at least about 1.2.

12. The cosmetic composition of claim 1, wherein the kaolin has a bulk density of at least about 150 g/l.

13. The cosmetic composition of claim 1, wherein the kaolin has a surface area of at least about 8 $m^2$/g.

14. The cosmetic composition of claim 1, wherein the cosmetic composition is a solid or liquid cosmetic composition.

15. The cosmetic composition of claim 1, wherein the kaolin has a surface area of at least about 15 $m^2$/g measured by BET nitrogen absorption.

\* \* \* \* \*